(12) United States Patent
Messer

(10) Patent No.: US 8,480,604 B2
(45) Date of Patent: Jul. 9, 2013

(54) CARBON FIBER ORTHOSIS AND ASSOCIATED METHOD

(76) Inventor: Bill Messer, Grand Rapids, MI (US)

( * ) Notice: Subject to any disclaimer, the term of this patent is extended or adjusted under 35 U.S.C. 154(b) by 1061 days.

(21) Appl. No.: 12/134,660

(22) Filed: Jun. 6, 2008

(65) Prior Publication Data

US 2008/0319361 A1    Dec. 25, 2008

Related U.S. Application Data

(60) Provisional application No. 60/942,446, filed on Jun. 6, 2007.

(51) Int. Cl.
*A61F 5/00* (2006.01)
*A61F 13/00* (2006.01)

(52) U.S. Cl.
USPC .......................... 602/6; 602/5; 602/8; 602/27

(58) Field of Classification Search
USPC . 602/6–10, 5, 27, 26; 156/285, 242; 264/101, 264/102, 220, 222
See application file for complete search history.

(56) References Cited

U.S. PATENT DOCUMENTS

| 6,146,344 | A | 11/2000 | Bader | |
|---|---|---|---|---|
| 7,749,423 | B2 * | 7/2010 | Bader | ........................... 264/511 |
| 2007/0073202 | A1 | 3/2007 | Bader | |

* cited by examiner

*Primary Examiner* — Kim M Lewis
(74) *Attorney, Agent, or Firm* — Robert Sayfie

(57) ABSTRACT

A method of making an orthoses, comprising the steps of preparing a plaster mold, upon which the layers of the orthosis will be placed and formed; and placing layers of material on the mold, then forming and removing the layers. An orthosis, comprising a footplate that is capable of receiving a human foot thereabove, a heel portion at the rear side of the footplate; a strut extending upwardly from the heel portion; a calf portion extending forwardly from the strut, the calf portion including a tibial shell; the tibial shell extends around the front of the user's tibia; a rear portion extends around the back of the user's calf a rear portion disposed rearwardly with respect to the calf portion; and sides such that the calf portion is completely circumferential without seams. Two foam layers line the orthoses for comfort and ease of use.

13 Claims, 11 Drawing Sheets

CARBON FIBER ORTHOSIS AND ASSOCIATED METHOD

RELATED APPLICATIONS

This application claims priority from U.S. provisional patent application No. 60/942,446, filed on Jun. 6, 2007.

BACKGROUND OF THE INVENTION

The present invention is directed to a method of making an orthoses (i.e., devices which support or correct the function of a limb or the torso), and more particularly to a carbon fiber ankle-foot orthosis, or orthotic, and to the structure of the orthosis.

In traditional Ankle Foot Orthotics (known in the art as "AFOs"), or Knee-Ankle Foot Orthotics ("KAFOs") the patient's ankle is usually fixed at 90 degrees by a thermoplastic or metal and leather AFO or KAFO to provide adequate clearance in swing phase of gait. In some cases, where the patient demonstrates active movement against gravity in the ankle, the traditional brace can only give dorsiflexion assist and can only assist or resist in one direction.

One particular disadvantage of these conventional AFO's is that patients may lose their active range of motion and/or lose all potential to gain active range of motion, if they do not move a muscle or joint for an extended period of time. By not moving in a natural pattern repetitive damage may occur to joints further up the chain. If the orthosis could allow for movement, assist/resist in both dorsiflexion and plantar flexion of the ankle at the same time a natural gait pattern could be produced similar to a non-affected limb.

SUMMARY OF THE INVENTION

The present invention provides a carbon fiber orthosis that enables natural movement to the foot, ankle, knee and hip during gait. The orthosis provides both dorsiflexion and plantar flexion assist of the ankle at the same time.

In one embodiment, the orthosis is an ankle-foot orthosis that includes at least one layer of carbon fiber that is impregnated with a resin and hardened into the shape of a desired limb or body part. In one embodiment, the orthosis includes a plurality of layers of carbon fiber fabric and a structural enhancer, such as a layer of braided carbon fiber tubing that is attached to the carbon fiber fabric. The braided carbon fiber tubing may be attached to the carbon fiber fabric by one or more layers of resin placed between the braided carbon fiber tubing and the carbon fiber fabric.

In another embodiment the orthosis includes a first layer of impregnated carbon fiber fabric, a second layer of impregnated carbon fiber fabric, a third layer of impregnated carbon fiber fabric, a layer of braided carbon fiber tubing adhered to the third layer of fabric, a fourth layer of impregnated carbon fiber fabric adhered to the braided carbon fiber tubing and the third layer of fabric, and a fifth layer of impregnated carbon fiber fabric. The layers of carbon fiber fabric may be either a unidirectional weave or a bidirectional weave, and in one embodiment, the layers alternate between unidirectional and bidirectional.

The orthosis is designed to be used most commonly with neuromuscular diseases to assist the musculoskeletal system in recreating what is missing from the nervous system.

In one embodiment, the types of pathologies that the orthosis is most commonly designed for are: Charcot-Marie-Tooth Neuropathy, Multiple Sclerosis, ALS, Traumatic Brain Injury, CVA with hemiparisis, Peripheral Neuropathies, Spinal Cord Injury, Cerebral Palsy, Spinal Bifida, Foot Drop, Weakness in Quadriceps, etc. In another embodiment, anyone with a Neuromuscular Condition that decreases function in the lower extremities can be a candidate for this new orthosis. Typically, if the patient has a grade 2 or less dorsiflexion strength the orthosis will fix the ankle at 90 degrees. The present invention allows for movement and actually assists and resists dorsiflexion and plantar flexion. If the patient has any deficits in proprioception and or strength in dorsiflexion, plantar flexion or quadriceps the present invention will provide the appropriate amount of support and still allow for a normal heel to toe progression. Since the present invention is custom molded and provides total contact wherever the carbon is located, it gives increased proprioception and correction of a joint (Ex. Foot and Ankle). The patient can have pes planus, and subtalar valgus or pes cavus and subtalar varus and be corrected to neutral. The footplate is total contact and contains varus/valgus corrective forces.

DETAILED DESCRIPTION OF THE CURRENT EMBODIMENT

I. Overview

This invention is a method of making an ankle-foot orthotic (AFO) orthosis, and a knee-ankle-foot orthotic (KAFO) orthosis.

Figure 1:
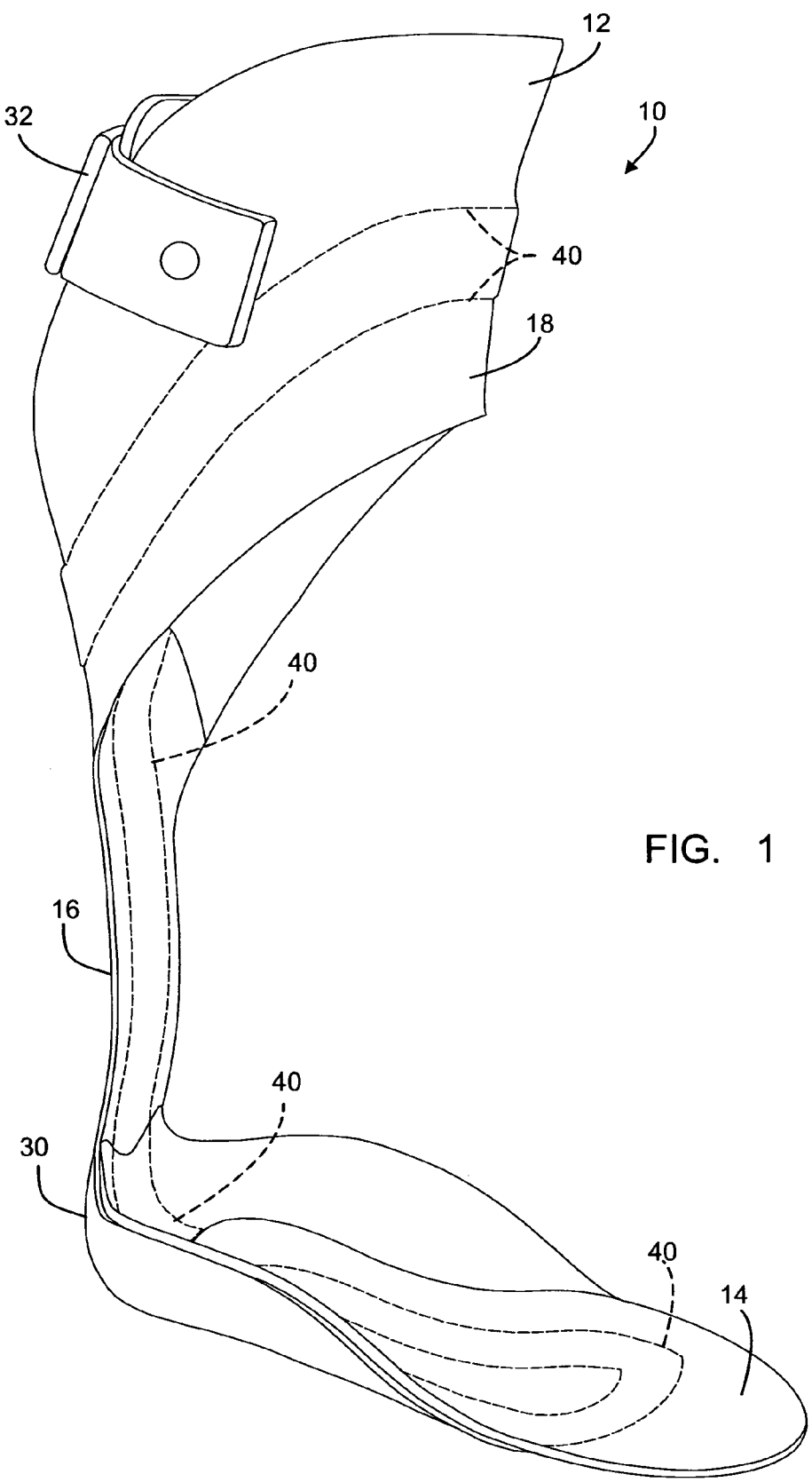
FIG. 1 is a pictorial of one embodiment of the present invention.
Figure 1A:
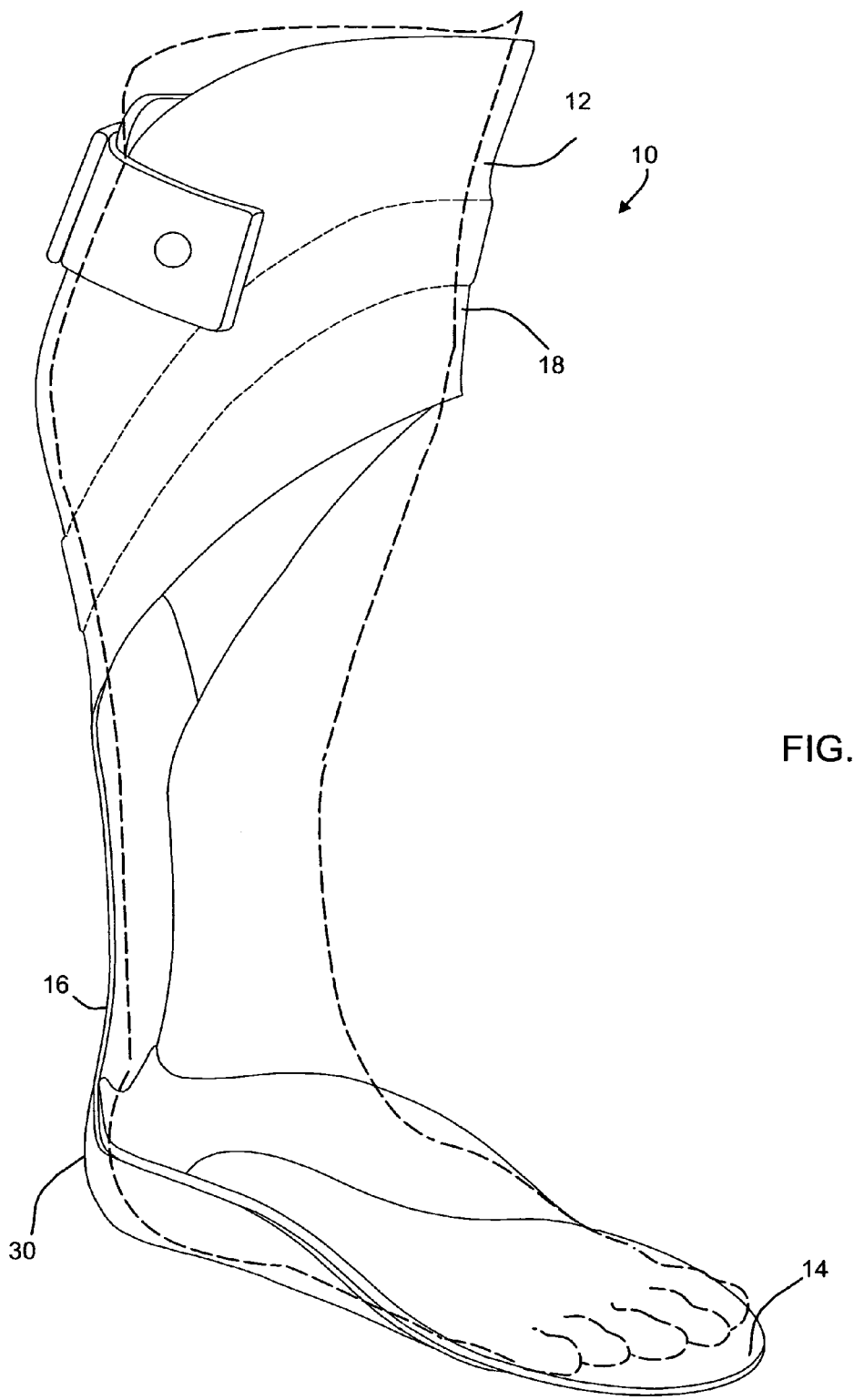
FIG. 1A is a pictorial of one embodiment of the present invention as it may be applied to a lower leg.
Figure 2:
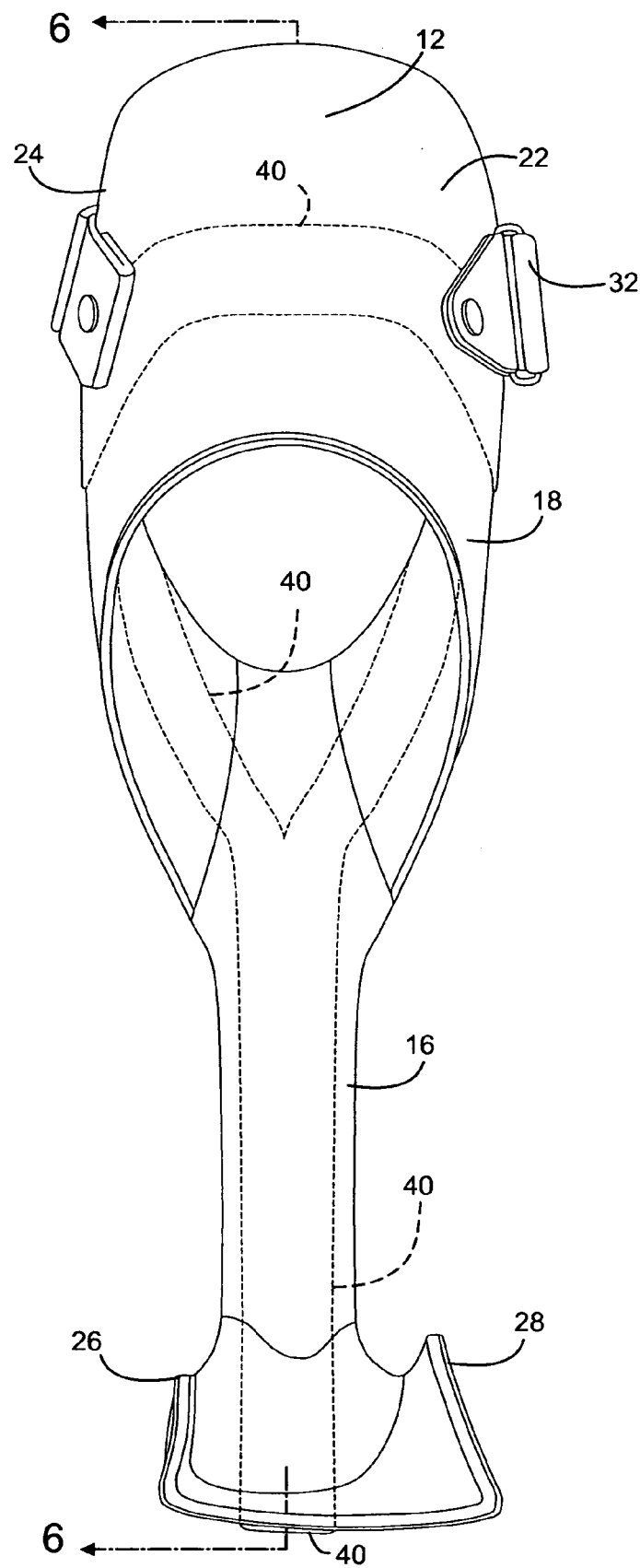
FIG. 2 is a pictorial of a front view of an embodiment of the present invention.
Figure 3:
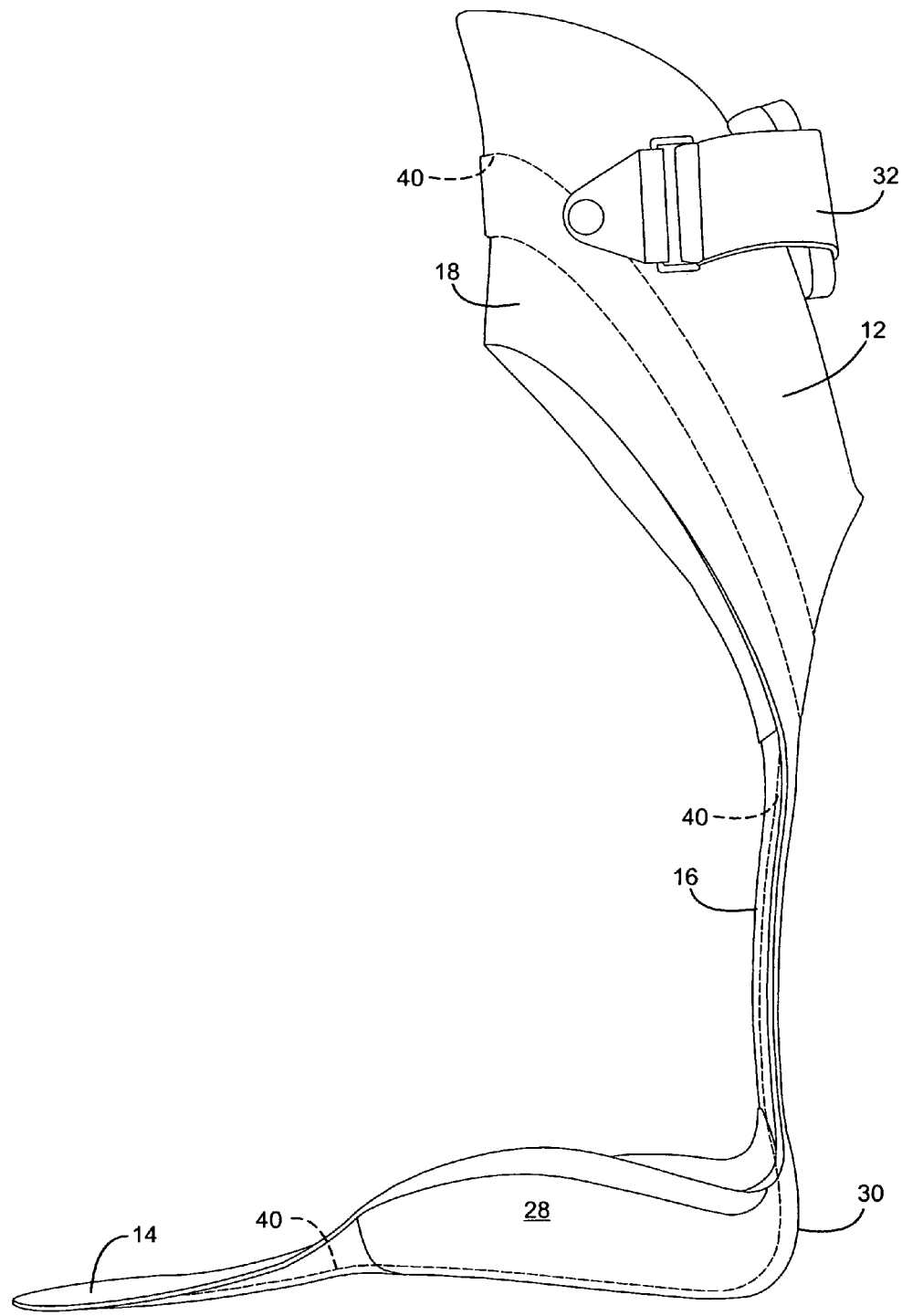
FIG. 3 is a pictorial of a side view of an embodiment of the present invention.
Figure 4:
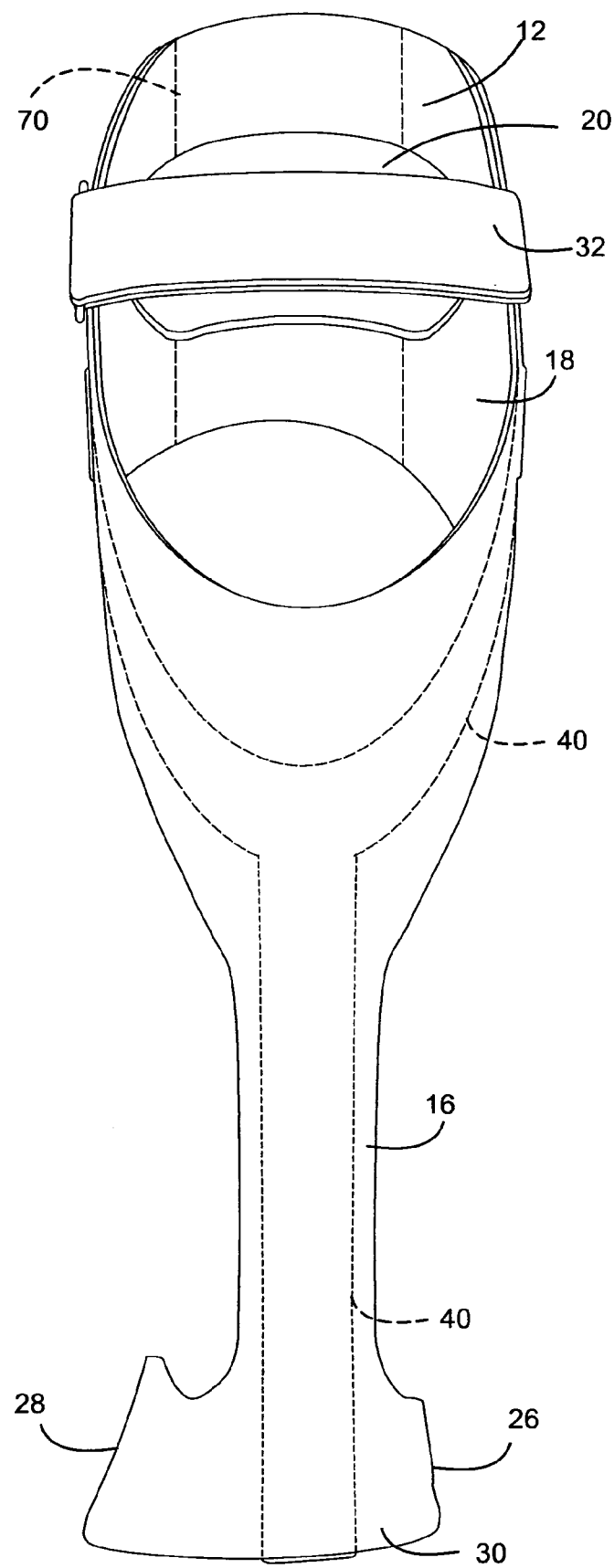
FIG. 4 is a pictorial of a rear view of an embodiment of the present invention.
Figure 5:
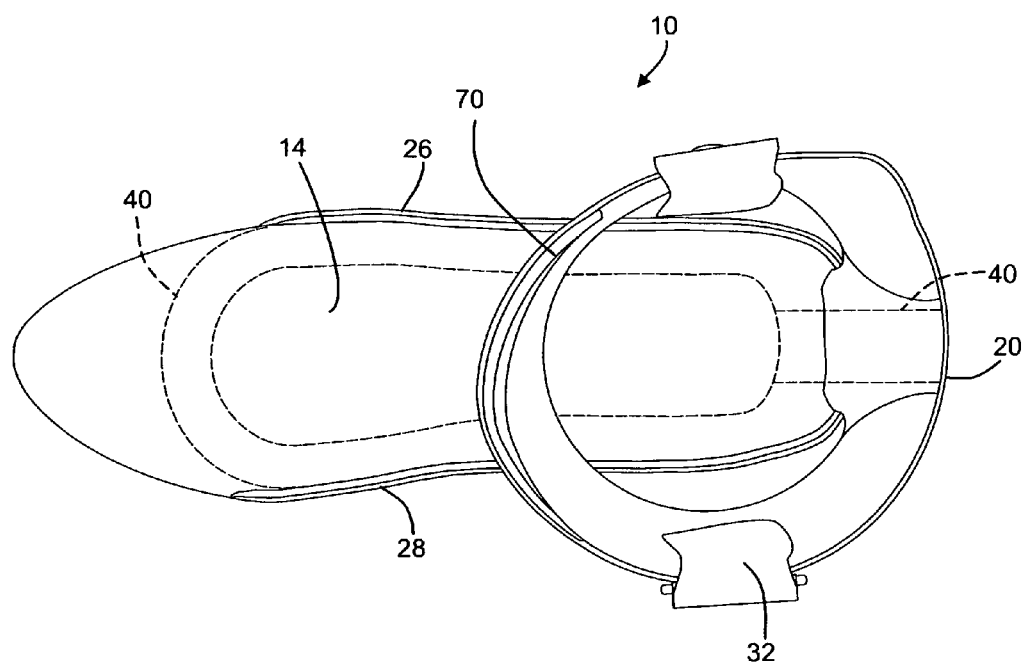
FIG. 5 is a pictorial of a top view of an embodiment of the present invention.
Figure 6:
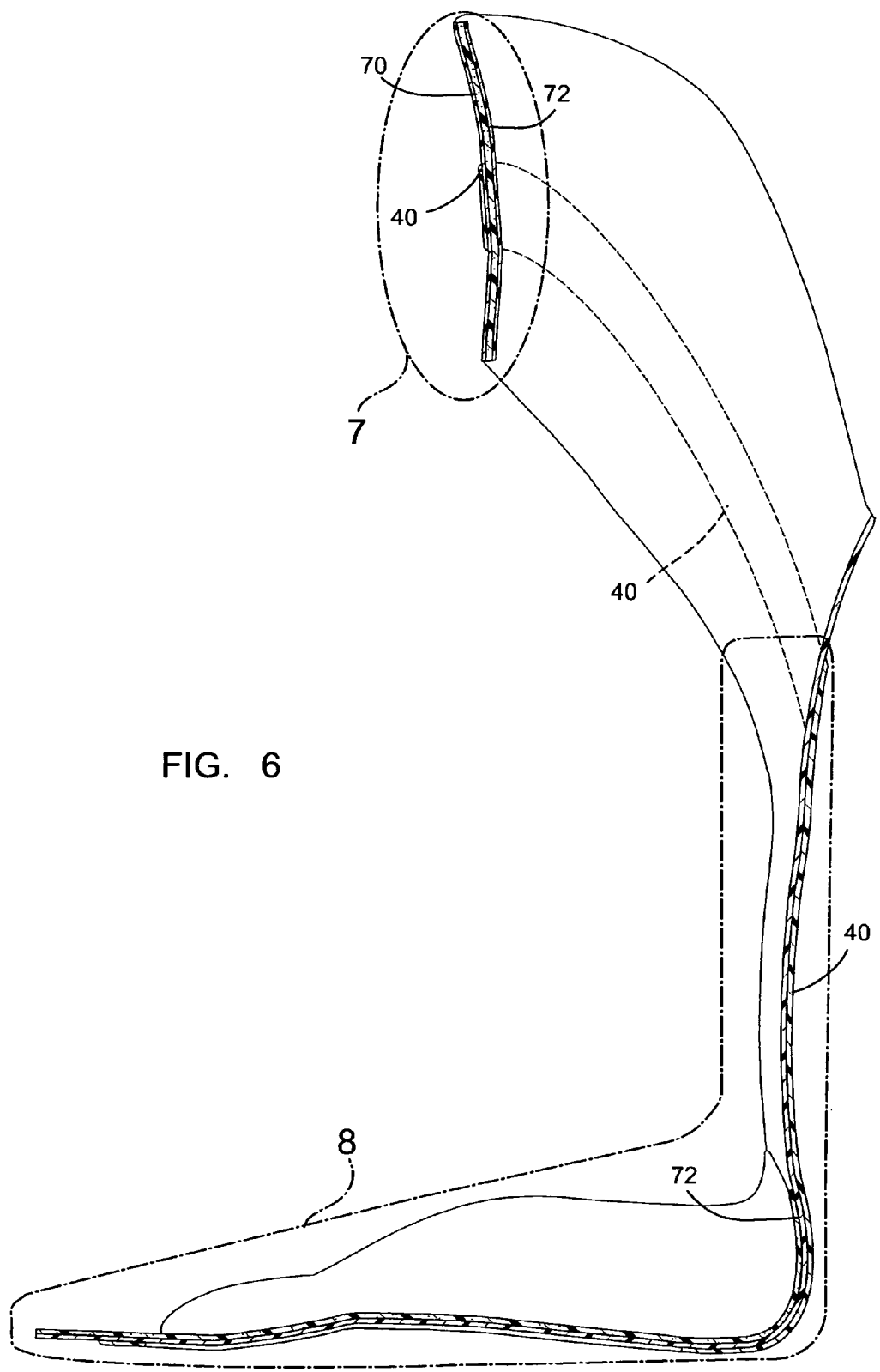
FIG. 6 is a pictorial of a an embodiment with the reinforcing foam illustrated.

FIG. 1 illustrates one embodiment of the present invention orthosis 10. This invention is also the apparatus or structure generally designated 10. Although the materials and associated method of the present invention could be used in connection with a wide variety of orthoses, for purposes of illustration, it will be described in connection with one embodiment, wherein the orthosis is an ankle-foot orthotic (AFO) orthosis 10. In another embodiment, the orthosis may be formed to fit a more extensive portion of a patient's leg that incorporates the patient's knee, a knee-ankle-foot orthotic (KAFO) orthosis 10. In yet another embodiment, the orthosis is formed to fit a completely separate feature of the patient's anatomy, such as a patient's torso.

II. Structure

As illustrated in FIGS. 1-9, The ankle-foot orthosis 10 generally includes a calf portion 12, footplate 14 and a strut 16 connecting the calf portion 12 and the footplate 14. In one embodiment, the entire orthosis 10 is molded to a shape that is customized to the particular shape of the leg of a particular user. The calf portion 12 includes a tibial shell 18 that extends around the front of the user's tibia, a rear portion 20 that extends around the back of the user's calf, and sides 22, 24 that extend along the sides of the user's leg, such that the calf portion is completely circumferential without seams. The footplate 14 extends under substantially all of the foot of the user, and includes lateral 26 and medial 28 flanges that extend upwardly on the sides of the user's foot, and a heel portion 30 that extends upwardly around the heel of the user's foot. The strut 16 extends between the calf portion 12 and the footplate 14. In the illustrated embodiment, the strut 16 is a generally straight strip of material that connects the heel portion 20 of the footplate 14 to the sides 22, 24 of the calf portion 12.

Figure 7:
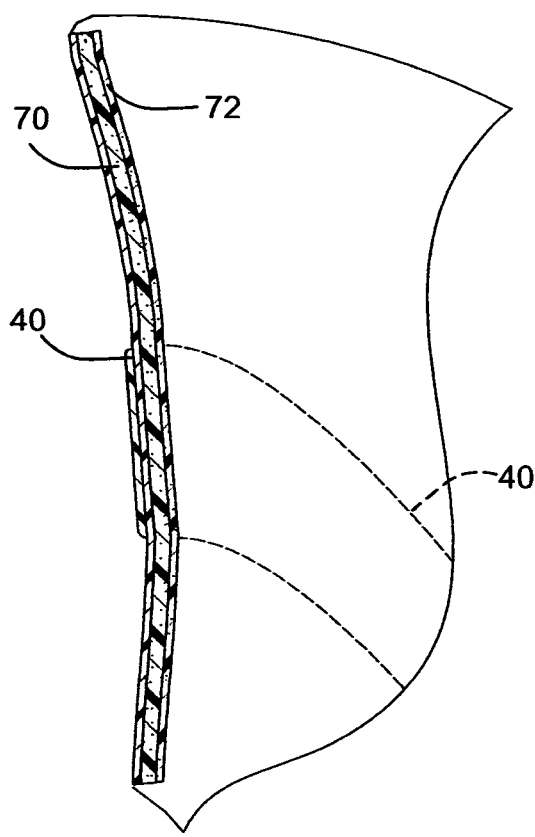
FIG. 7 is a pictorial of an exploded view from FIG. 6, illustrating the standard foam and the reinforcing foam.

FIG. 7 illustrates an embodiment having two levels of varying foam. A standard foam 72 is nearest the leg of the user, which the user's skin may contact and is more pliable and softer than the reinforcing foam 70. The reinforcing foam 70 enables the standard foam 72 to flex and move, without hitting a hard firm surface, which would cause the user pain and discomfort. The reinforcing foam 70 may be applied to the carbon fiber material, and the standard foam 72 may be applied to the reinforcing foam 70 via an adhesive. The standard foam 72 disposed in the contactable area, which is an area where the user's skin or leg may contact the orthoses, so that the user's skin contacts the standard foam 72 during use, and a reinforcing foam 70 disposed between the standard foam 72 and at least one of said footplate 14, said heel portion 30, said strut 16, said heel portion 30, said calf portion 12, or said tibial shell 18.

Figure 8:
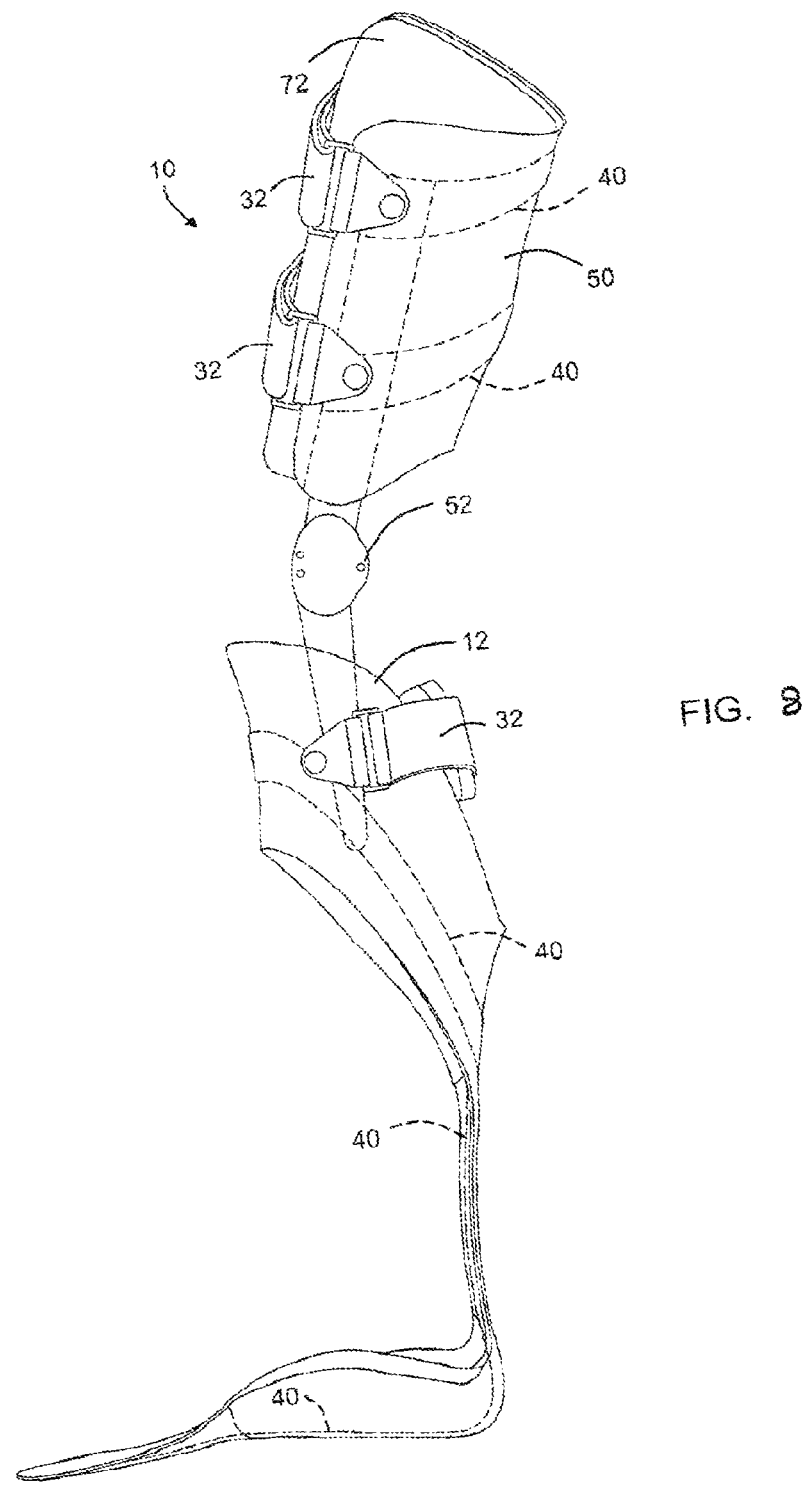
FIG. 8 is a pictorial of an embodiment of the present invention with a knee member, to form a knee-ankle-foot orthotic ("KAFO").
Figure 9:
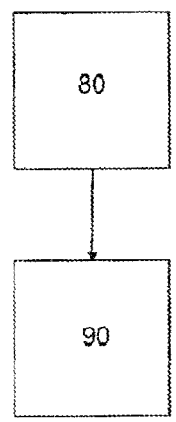
FIG. 9 is a block diagram of an embodiment of a method of making the present invention.
Figure 10:
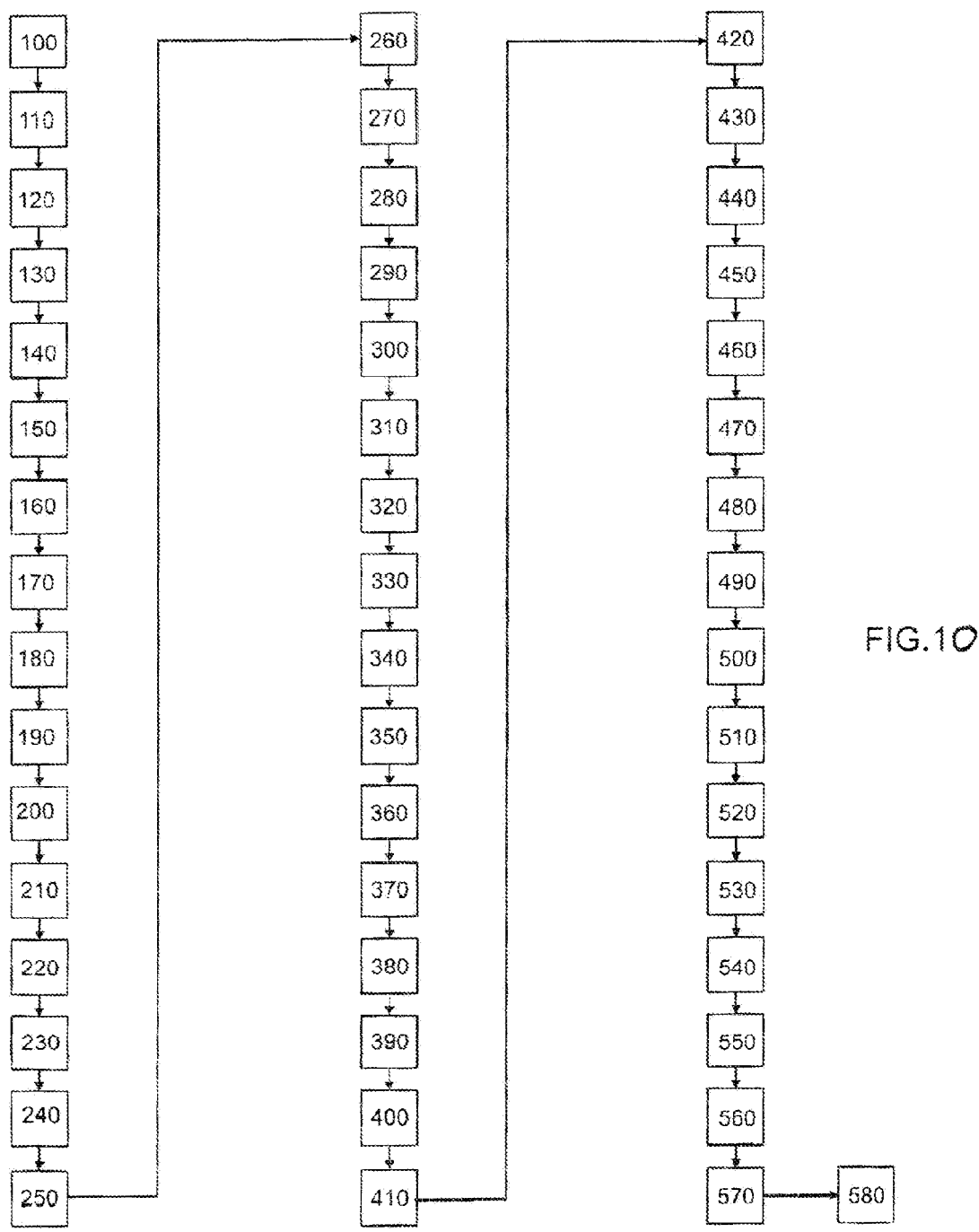
FIG. 10 is a block diagram of an embodiment of a method of making the present invention.

FIG. 8 illustrates a knee-ankle-foot orthosis (KAFO), which is essentially the AFO of the present invention, with the knee member 50 movably connected to the AFO of the present invention via a movable joint 52.

In one embodiment, the entire orthosis is formed from a layer or layers of hardened carbon, graphite or Kevlar fiber fabric, such as a woven carbon fiber fabric that is pre-impregnated with an epoxy resin and hardened on a mold in an oven. The carbon fiber fabric may be a bidirectional weave, a unidirectional weave, or an alternative weave or arrangement. One example of a bidirectional weave may be a type manufactured by Mapewrap, and called MAPEWRAP C BI-AX. One type of unidirectional weave may be a type manufactured by Mapewrap, and called MAPEWRAP C UNI-AX. These types of products may be found at http://www.directindustry.com/prod/mapei/carbon-fiber-fabric-33942-197584.html.

In embodiments that include multiple layers of the pre-impregnated fabric, the resin of the various layers is bonded together during a heating process under intense vacuum. The orthosis 10 may further include a layer or layers of carbon, graphite or Kevlar fibers in a braided tubular form 50, referred to as a "g-braid." The g-braid 40 used may have one of a variety of widths, ranging from about ⅜" to about 6". In one embodiment, the orthosis additionally includes a layer or layers of resin sheets, often referred to as "ready preg," that are comprised of a hardened sheet of an epoxy resin. The ready preg sheets may be placed, for example, above and below the layers of g-braid 40, such that the ready preg flows into and through the g-braid 40 during the heating and curing process to attach the g-braid 40 to the other layers. In one embodiment, a sheet of ready preg is rolled up and inserted into a g-braid 40 tube to provide an additional bond between the layers. The sheets of ready preg are typically frozen sheets that are melted into the fabric layers when the orthosis is heated.

In the illustrated embodiment, the orthosis 10 includes a particular arrangement of the above noted materials, including a first layer of bidirectional pre-impregnated carbon fiber fabric on the calf portion 12, strut 16 and footplate 14; a second layer of unidirectional pre-impregnated carbon fiber fabric on the calf portion 12, strut 16 and footplate 14; a third layer of bidirectional pre-impregnated carbon fiber fabric located only on the strut; a layer of ready preg on the calf portion 12, strut 16, and footplate 14; a layer of 1" g-braid 40 on the calf portion 12 and the strut 16; a layer of g-braid 40 on the strut 16, around the footplate 14 and up to the back of the calf portion 12, with a sheet of ready preg inserted into the g-braid 40 tube on the strut 16; a layer of ready preg over all of the g-braid 40; a fourth layer of unidirectional pre-impregnated carbon fiber fabric on the strut 16 only; and a fifth layer of bidirectional pre-impregnated carbon fiber fabric on the calf portion 12, strut 16 and footplate 14.

The arrangement and layering of the orthosis materials of the present invention is important in this orthosis due to the carbon fiber spring that is fabricated. In a sense the strut 16—or posterior beam—effectively forms a large spring. The spring has to have enough strength not to break, but yet enough flexibility to allow natural movement. This is achieved by adding more or less layers dependent upon the patient's height, weight, and strength. In one embodiment, the orthosis is fabricated with a beam that is stronger than needed, and trimmed narrower to make it more flexible as desired. This makes the strut adjustable even though it does not incorporate ankle joints.

III. Method of Manufacture

An orthosis according to one embodiment of the present invention is manufactured using the following steps, which are broken down into two sections. First, preparing a plaster mold 80, upon which the layers of the orthosis will be placed and formed. Second, placing layers of material on the mold, then forming and removing the layers.

Preparation of the Plaster Mold

This step 80, which may include preparing the plaster mold 80, may have the following steps:

1. Creating a molded plaster or fiberglass cast 100.
   Creating a molded plaster or fiberglass cast 100 is performed by creating a molded plaster or fiberglass cast 70 in the shape of the feature of the patient's anatomy upon which the orthosis is intended to be used. In one embodiment, this may be applicable to the lower portion of a patient's leg, including the ankle and the foot.
2. Stapling and sealing the cast with plaster bandage 110.
3. Setting the cast such that the angle between the foot portion and the leg portion is approximately 90 degrees (depending upon heel height of shoe) 120.
4. Sealing the cuts in the cast with the cast angled at about 90 degrees 130.
5. Filling the cast with plaster, and then allowing the plaster mold to set 140.
6. Stripping the initial cast away from the newly formed plaster mold 150.
7. Smoothing the plaster mold with sheer forms and a sanding screen 160.
8. Marking the finish height and heights for back of the orthosis directly on the plaster mold 170.
9. Drawing trim lines indication the dimensions of the orthosis directly on the plaster mold 180. In one embodiment, the front tibia shell (i.e., the calf portion 12 of the orthosis that extends around the front of the tibia) should be 3.5" to 4", the sides of orthosis should be about 3.5" wide, and the strut is about 2" wide.

10. Laying plaster bandage on the drawn trim line 190. This may build up the mold at the areas near the trim lines-resulting in flared edges in the final orthosis.
11. Applying liquid plaster on the plaster bandage 200 to make all holes and valleys level.
12. Squaring off the portions of the mold in the area of the footplate and build up the portions of the mold in the area of the medical wall of the orthosis and the lateral wall of the orthosis 210.
13. Sanding the entire mold 220 so that it is smooth and everything has a smooth transition.
14. Recasting the modified leg mold 230 by pulling a cotton stockinet or similar material over the leg, then wrap leg with fiberglass wrap, let the wrap harden, then cut the wrap off of the leg mold.
15. Heating and pulling a foam padding material over the calf portion of the leg mold and affixing the foam to the mold 240.
16. Cutting the foam away from the strut 250, so that it doesn't cover any part of the strut.
17. Skiving the foam so that it tapers down to the plaster mold, and then skiving the foam in the area of the footplate 260 before pulling it on the plaster mold.
18. Heating the foam in the area of the footplate and pull the heated foam over the foot plate, affixing or stapling the foam to the footplate 270.
19. Wrapping a clear plastic wrap (such as conventional kitchen plastic wrap) over the entire orthosis, including over the foam 280.
20. Tracing the trim lines drawn on the mold onto a material that is placed on the mold 290, such as a piece of paper, to create a pattern that can be used to cut layers of the orthosis to appropriate sizes. This will ensure the necessary amount of material is used in creating the orthosis, minimizing waste.

Lay Up of the Materials Forming the Orthosis

This step 90 may include placing layers of material on the mold, then forming and removing the layers described below.

1. Applying a layer of bidirectional carbon fiber fabric over the calf, strut and footplate areas of the mold 300, and over the foam. The layer of carbon fiber fabric may be pre-impregnated with resin.
2. Placing a layer of unidirectional carbon fiber fabric over the calf, strut and footplate 310. The layer of carbon fiber fabric may be impregnated with resin.
3. Applying a layer of bidirectional carbon fiber fabric in the strut 320. When included, this layer may increase the strength of the strut, and enhance the assist characteristics of the orthosis for both dorsiflexion and plantar flexion. The layer of carbon fiber fabric may be impregnated with resin.
4. Placing a sheet of resin material 102, such as Ready Preg, around the calf, down the strut and around the footplate 330.
5. Applying a 1" g-braid 40 (a braided, tubular carbon fiber fabric) around the calf and cut at the strut 340.
6. Placing a 1" g-braid 108 down the strut, around the footplate, and back up to the back of the calf 350. When the g-braid 40 in steps 5 and 6 is included, it may increase the strength of the orthosis in the areas that it is placed, and enhance the assist characteristics of the orthosis for both dorsiflexion and plantar flexion.
7. Sliding a sheet of resin down inside the tubular g-braid 40 on the strut only 360.
8. Applying a sheet of resin 110 over all exposed g-braid 370, making sure that all of the g-braid 40 is covered, or at least that most of the g-braid 40 is covered.
9. Placing a layer of bidirectional carbon fiber fabric over the calf, strut and footplate 380. The layer of carbon fiber fabric may be impregnated with resin.
10. Applying a layer of bidirectional carbon fiber fabric over the calf, strut and footplate 390. The layer of carbon fiber fabric may be impregnated with resin.
11. Wrapping the orthosis with clear plastic wrap about 3 to 6 times 400.
12. Creating holes through the plastic wrap along the g-braid in the calf, strut and footplate 410.
13. Pulling a shear nylon stockinet over entire orthosis twice 420.
14. Pulling a thicker (thicker than the shear nylon stockinet in step 420) nylon stockinet over entire orthosis twice 430.
15. Moving the orthosis to roto lam rack and pull a plastic bag over the orthosis, sealing it so that it is air tight 440.
16. Placing the wrapped orthosis into a vacuum chamber oven 200, and turn on the vacuum, making sure that there is no air leaks 450.
17. Heating orthosis for approximately 4 hours at about 250° F. 460.
18. Testing orthosis by applying pressure, such as with thumb to make sure that orthosis is done and there are no soft spots 470.
19. Pulling orthosis out of oven pulling all layers of plastic and nylon stocking off of orthosis 480.
20. Breaking orthosis off of the plaster mold 490.
21. Smoothing or sanding orthosis down to the trim lines and rough up the outside surface 500.
22. Cleaning off all extra dust and materials with water 510.
23. Mixing two-part epoxy at about a 1 to 1 ration 520.
24. Applying epoxy to clean orthosis let stand for about 24 hours 530.
25. Sanding down all extra epoxy 540.
26. Cutting out pads out of foam for the calf and footplate 550.
27. Skiving calf edges and footplate next to the heel 560.
28. Sanding down all edges so that foam and calf and footplate are level or flush 570.
29. Attaching a strap to the back of the calf 580.

The above method of manufacture is used in the formation of one embodiment of the present invention, wherein the orthosis includes five layers of carbon fiber fabric. This embodiment has been proven through testing to provide a high degree of strength, and very low weight, such that it is useful for a wide range of patient types. Alternative embodiments of the present invention are possible, and may vary the number of layers, the particular arrangement of bidirectional and unidirectional layers and the use and location of the g-braid 40 and the sheets of resin. The use of additional layers of carbon—either in fabric sheet form or braided form—increases the strength of the orthosis in the areas where the additional carbon is placed. The use of additional layers of resin sheets increases the bond between the various layers of carbon, especially in the specific areas in which the resin sheets are placed. In embodiments where the carbon fiber fabric or g-braid is pre-impregnated with resin, the resin sheets also bond with the impregnated resin during the heating process. In an alternative embodiment, wherein the carbon fiber fabric is not pre-impregnated with resin, sheets of resin may be placed between each layer of carbon fiber fabric to attach the layers together. In another alternative embodiment, the layers may be attached by another known method, such as wet lamination.

The variations in layers of carbon, g-braid 40, and adhesive in the area of the strut are generally determined by starting with the embodiment noted in the above method (i.e., 5 layers of pre-impregnated carbon fiber, arranged bi-uni-bi-uni-bi, with one g-braid 40 down the center of the strut, including a sheet of resin inside the g-braid 40). This is base line from for 50 lbs and 42 inches tall to 165 lbs and 5 foot ten inches. As the need arises to add layers for activity levels and height and weight it is imperative that the clinician evaluates through gait analysis forces to determine if more layers are required. (Example: golfing adds more stress to the spring of carbon fiber and requires more reinforcement). In one embodiment, if the patient is greater than 165 lbs and 5"10, another layer of g-braid 40 is inserted inside of the original braid (a tube within a tube) and add more resin (typically ready-preg resin). In another embodiment, if additional reinforcement is needed, one more layer of uni and one more layer of bi may be added, making the orthosis 7 layers of carbon fiber fabric and 2 layers of g-braid 40. This embodiment is suitable for patients up to 300 lbs., and 6'7" tall.

The above descriptions are those of current embodiments of the invention. Various alterations and changes can be made without departing from the spirit and broader aspects of the invention.

I claim:

1. A method of making an orthosis, comprising the steps of:
   preparing a plaster mold (80), upon which layers of the orthosis will be placed and formed;
   placing layers of material on the mold, then forming and removing the layers (90) creating a molded plaster or fiberglass cast (100);
   stapling and sealing the cast with plaster bandage (110);
   setting the cast such that an angle between a foot portion and a leg portion is approximately 90 degrees (120);
   sealing the cuts in the cast with the cast angled at about (90) 90 degrees (130);
   filling the cast with plaster, and then allowing the plaster mold to set (140);
   stripping the cast away from a newly formed plaster mold (150);
   smoothing the plaster mold with sheer forms and a sanding screen (160);
   marking a finish height and heights for a back of the orthosis directly on the plaster mold (170);
   drawing trim lines indicating dimensions of the orthosis directly on the plaster mold (180);
   applying liquid plaster on a plaster bandage (200);
   squaring off portions of the mold in an area of a footplate and building up portions of the mold in an area of a medial wall of the orthosis and a lateral wall of the orthosis (210);
   sanding the entire mold (220) so that it is smooth;
   recasting a modified leg mold (230;
   heating and pulling a foam padding material over a calf portion of the leg mold and affixing the foam padding material to the mold (240);
   cutting the foam padding material away from a strut (250);
   skiving the foam padding material so that it tapers down to the plaster mold, and then skiving the foam padding material in the area of the footplate before pulling it on the plaster mold (260);
   heating the foam padding material in the area of the footplate and pulling the heated foam padding material over the footplate, affixing or stapling the foam padding material to the footplate (270);
   wrapping a clear plastic wrap over the orthosis, including over the foam padding material (280); and
   tracing trim lines drawn on the mold onto a material that is placed on the mold (290).

2. The method of claim 1, wherein said step of creating a molded plaster or fiberglass cast (100) is performed by creating a molded plaster or fiberglass cast (70) in the shape of the feature of the patient's anatomy upon which the orthosis is intended to be used.

3. The method of claim 2, wherein the patient's anatomy is the lower portion of a patient's leg, including the ankle and the foot.

4. The method of claim 1, wherein a front tibia shell should be 3.5" to 4", the sides of orthosis should be about 3.5" wide, and the strut is about 2" wide, and laying plaster bandage on the drawn trim line (190).

5. The method of claim 1, wherein step (230) further includes pulling a cotton stockinet or similar material over the leg, then wrap leg with fiberglass wrap, let the wrap harden, then cut the wrap off of the leg mold.

6. The method of claim 1, wherein the cutting step (250) is performed so that the foam is cut so that it does not cover any part of the strut.

7. The method of claim 1, wherein the material in the tracing step (290) is a piece of paper, to create a pattern that can be used to cut layers of the orthosis to appropriate sizes, ensuring the necessary amount of material is used in creating the orthosis, minimizing waste.

8. A method of making an orthoses, comprising the steps of:
   preparing a plaster mold (80), upon which layers of the orthosis will be placed and formed;
   placing layers of material on the mold, then forming and removing the layers (90);
   wherein the step of placing layers of material on the mold, then forming and removing the layers (90), further comprises:
   applying a layer of bidirectional carbon fiber fabric over a calf, a strut and footplate areas of the mold and over a foam (300);
   placing a layer of unidirectional carbon fiber fabric over the calf, strut and footplate (310);
   applying a layer of bidirectional carbon fiber fabric in the strut (320);
   placing a sheet of resin material (102) around the calf, down the strut and around the footplate (330);
   applying a 1" g-braid around the calf and cut at the strut (340);
   placing a 1" g-braid down the strut, around the footplate, and back up to the back of the calf (350);
   applying a sheet of resin (110) over all exposed g-braid (370);
   placing a layer of bidirectional carbon fiber fabric over the calf, strut and footplate (380);
   applying a layer of bidirectional carbon fiber fabric over the calf, strut and footplate (390);
   wrapping the orthosis with clear plastic wrap about 3 to 6 times (400);
   creating holes through the plastic wrap along the g-braid in the calf, strut and footplate (410);
   pulling a shear nylon stockinet over entire orthosis twice (420);

pulling a thicker nylon stockinet over entire orthosis twice (430);

moving the orthosis to a roto lam rack and pull a plastic bag over the leg, sealing it so that it is air tight (440);

placing the wrapped orthosis into a vacuum chamber oven (200), and turning on the vacuum, making sure that there are no air leaks (450);

heating the orthosis for approximately 4 hours at about 250° F. (460);

testing the orthosis by applying pressure, such as with thumb to make sure that orthosis is done and there are no soft spots (470);

pulling the orthosis out of oven, pulling all layers of plastic and nylon stocking off of orthosis (480);

breaking the orthosis off of the plaster mold (490);

smoothing or sanding the orthosis down to the trim lines and roughing up the outside surface (500);

cleaning off all extra dust and materials with water (510);

mixing two-part epoxy at about a 1 to 1 ratio (520);

applying epoxy to the clean orthosis, letting it stand for about 24 hours (530);

sanding down all extra epoxy (540);

cutting out pads out of foam for the calf and footplate (550);

skiving calf edges and footplate next to a heel portion (560);

sanding down all edges so that foam and the calf and footplate are level (570); and attaching a strap to the back of the calf (580).

9. The method of claim 8, wherein the bidirectional carbon fiber fabric is pre-impregnated with resin.

10. The method of claim 8, wherein the unidirectional carbon fiber fabric is impregnated with resin.

11. The method of claim 8, wherein the bidirectional carbon fiber fabric in the strut of the applying step (320) increases the strength of the strut, and enhances the assist characteristics of the orthosis for both dorsiflexion and planar flexion.

12. The method of claim 8, wherein in the applying step of (340) and the placing step of (350), the g-braids increase the strength of the orthosis in the areas that it is placed, and enhance the assist characteristics of the orthosis for both dorsiflexion and plantar flexion.

13. The method of claim 8, wherein the applying step (370) is performed by making sure that at least that most of the g-braid is covered with the sheet of resin (110).

* * * * *